(12) United States Patent
Kim et al.

(10) Patent No.: US 7,679,281 B2
(45) Date of Patent: Mar. 16, 2010

(54) LIGHT EMITTING DEVICE HAVING VARIOUS COLOR TEMPERATURE

(75) Inventors: Do Hyung Kim, Ansan-si (KR); Hyuck Jung Choi, Ansan-si (KR)

(73) Assignee: Seoul Semiconductor Co., Ltd., Seoul (KR)

( * ) Notice: Subject to any disclaimer, the term of this patent is extended or adjusted under 35 U.S.C. 154(b) by 226 days.

(21) Appl. No.: 12/051,637

(22) Filed: Mar. 19, 2008

(65) Prior Publication Data
US 2008/0231214 A1   Sep. 25, 2008

(30) Foreign Application Priority Data
Mar. 19, 2007   (KR) ................. 10-2006-0026750

(51) Int. Cl.
*H01L 33/00* (2006.01)
(52) U.S. Cl. .................... 313/501; 313/502; 257/98
(58) Field of Classification Search .............. 257/88, 257/89, 98, E33.061, E33.055; 313/498, 313/501, 502, 503, 504, 505; 315/246, 291; 362/84, 800
See application file for complete search history.

(56) References Cited

U.S. PATENT DOCUMENTS

| 6,577,073 B2 * | 6/2003 | Shimizu et al. ............. 315/246 |
| 7,075,225 B2 * | 7/2006 | Baroky et al. ............... 313/503 |

* cited by examiner

*Primary Examiner*—David Hung Vu
(74) *Attorney, Agent, or Firm*—H.C. Park & Associates, PLC

(57) ABSTRACT

A light emitting device capable of emitting light having various color temperatures is disclosed. The light emitting device includes a first light emitting part emitting a daylight color having a color temperature of 6000 K or more, a second light emitting part emitting white light having a color temperature less than 6000 K, and a third light emitting part emitting light in a visible range of 580 nm or more. The second and third light emitting parts are operable independently of the first light emitting part, and realize a warm white color having a color temperature of 3000 K or less with the white light emitted from the second light emitting part and the light emitted from the third light emitting part. The light emitting device realizes white light of various spectra and color temperatures corresponding to desired mood and utility. The light emitting device is controlled to emit light having a suitable wavelength or a suitable color temperature depending on the circadian rhythm of human, thereby enabling improvement of the user's health.

18 Claims, 6 Drawing Sheets

LIGHT EMITTING DEVICE HAVING VARIOUS COLOR TEMPERATURE

CROSS-REFERENCE TO RELATED APPLICATION

This application claims priority to Korean Patent Application No. 10-2007-0026750, filed Mar. 19, 2007, the contents of which are incorporated herein by reference in their entirety.

FIELD OF THE INVENTION

The present invention relates to a light emitting device, and more particularly to a light emitting device that includes a plurality of light emitting parts in a single package to realize a variety of spectra and color temperatures.

BACKGROUND OF THE INVENTION

Light Emitting Diodes (LEDs) refer to a semiconductor diode that emits light via generation and recombination of carriers, i.e. electrons and holes, in P-N junctions of a compound semiconductor. The LED consumes less power and has several to several dozen times the lifespan of conventional light bulbs or fluorescent lights, thereby being highly advantageous in terms of power reduction and durability. Additionally, the LED can be placed in a narrow space and is resistant to vibration. LED-based light emitting devices are used as display devices and backlights, and research is under way to apply them to general lighting. In recent years, white LEDs have come out in the marketplace, adding to already-available monochromatic LEDs, such as red LEDs, blue LEDs, and green LEDs. White LED-based light emitting devices are expected to experience rapidly increased demand along with an increase in application of such light emitting devices to automobile products, lighting products, and the like.

Humans have a circadian rhythm in which the physiological process is repeated in a roughly-24-hour cycle. For example, cortisol and melatonin, known as the "stress hormone" and the "sleep hormone," respectively, have a great influence on physical activity and sleeping, respectively. As a basis of daily physical activity, the level of cortisol undergoes diurnal variation with an increased level during the daytime and the lowest level occurring around midnight. On the other hand, the level of melatonin acting as hormone for midnight sleeping decreases during the daytime and increases at night, thereby promoting healthy levels of sleep while preventing drowsiness during the daytime.

Light generally affects such a physiological rhythm in humans, and sunlight in particular has a very great influence on humans. The color temperature of sunlight is higher than 6000 K before noon and gradually decreases afternoon. Color temperature is a physical value of color of a light source measured in degrees Kelvin (K). As the color temperature increases, the light source radiates blue light, and, as the color temperature decreases, the light source radiates strong red-yellow light. Additionally, a higher color temperatures facilitate increased brain activity and concentration, whereas a lower color temperature facilitates reasoning and relaxation.

As such, light provides various feelings and great influences on the physiological rhythms depending on the wavelengths and color temperature thereof, while causing various disorders, such as impaired digestion, chronic fatigue, and the like, in the case of failing to properly accommodate to variation of the light. Accordingly, various efforts have been made to develop lighting devices which can operate in consideration of the circadian rhythm of humans.

A conventional LED-based light emitting device employs various means for achieving white light emission. Generally, phosphors are disposed around an LED chip such that white light can be obtained by mixing some of primary emission light from the LED with secondary emission light having undergone wavelength conversion through the phosphors. Examples of phosphors for realizing white light emission include garnet phosphors, thiogallate, sulfide, silicate, oxynitride, and the like. However, when the light emitting devices employs such phosphors, there are disadvantages of a narrow range in color temperature, a very low color rendering index, and instability of a lamp. In other words, it is difficult to manufacture a light emitting device capable of providing various spectra or color temperatures. Furthermore, since red-based phosphors have a lower photo efficiency, it is necessary to increase power and the amount of phosphors in order to realize white light having a lower color temperature with a blue or ultraviolet-LED chip and the phosphors.

The present invention is conceived to solve the problems of the conventional techniques as described above, and it is an aspect of the present invention to provide a light emitting device that includes a plurality of light emitting parts in a single package to realize white light of various spectra and color temperatures.

It is another aspect of the present invention to provide a light emitting device, the spectrum and color temperature of which is capable of being adjusted depending upon the physiological rhythms of human.

It is a further aspect of the present invention to provide a light emitting device capable of realizing white light having a lower color temperature without significantly increasing power and phosphors.

In accordance with an aspect of the present invention, the above and other features of the present invention can be accomplished by the provision of a light emitting device capable of emitting light having various color temperatures. The light emitting device includes a first light emitting part, a second light emitting part, and a third light emitting part. The first light emitting part includes a first LED chip and a first phosphor, and emits a daylight color having a color temperature of 6000 K or more; the second light emitting part includes a second LED chip and a second phosphor, and emits white light having a color temperature less than 6000 K; and the third light emitting part includes a third LED chip which emits light in a visible range of 580 nm or more. The second and third light emitting parts are operable independently of the first light emitting part and realize a warm white color having a color temperature of 3000 K or less with the white light emitted from the second light emitting part and the light emitted from the third light emitting part.

The first or second light emitting part may comprise a phosphor represented by the following Chemical Formula 1:

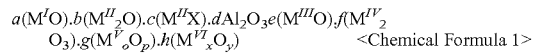
$a(M^IO).b(M^{II}_2O).c(M^{II}X).dAl_2O_3 e(M^{III}O).f(M^{IV}_2O_3).g(M^V_oO_p).h(M^{VI}_xO_y)$ <Chemical Formula 1>

(where $M^I$ is at least one selected from the group consisting of Pb and Cu; $M^{II}$ is at least one selected from the group consisting of Li, Na, K, Rb, Cs, Au, and Ag; $M^{III}$ is at least one selected from the group consisting of Be, Mg, Ca, Sr, Ba, Zn, Cd, and Mn; $M^{IV}$ is at least one selected from the group consisting of Sc, B, Ga, and In; $M^V$ is at least one selected from the group consisting of Si, Ge, Ti, Zr, Mn, V, Nb, Ta, W, and Mo; $M^{VI}$ is at least one selected from the group consisting of Bi, Sn, Sb, Sc, Y, La, Ce, Pr, Nd, Pm, Sm, Eu, Gd, Tb, Dy, Ho, Er, Tm, Yb, and Lu; X is at least one selected from the group consisting of F, Cl, Br, and I; and a, b, c, d, e, f, g, o, p, h, x, and y are respectively set in the ranges of: $0<a\leq2$, $0\leq b\leq2$, $0 \leq c \leq 2$, $0 \leq d \leq 8$, $0 \leq e \leq 4$, $0 \leq f \leq 3$, $0 \leq g \leq 8$, $1 \leq o \leq 2$, $1 \leq p \leq 5$, $0 \leq h \leq 2$, $1 \leq x \leq 2$, and $1 \leq y \leq 5$)

The first or second light emitting part may comprise a phosphor represented by the following Chemical Formula 2:

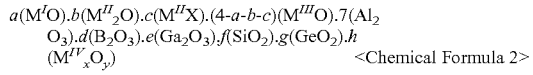

$a(M^I O).b(M^{II}_2 O).c(M^{III} X).(4-a-b-c)(M^{III} O).7(Al_2 O_3).d(B_2 O_3).e(Ga_2 O_3).f(SiO_2).g(GeO_2).h(M^{IV}_x O_y)$ <Chemical Formula 2>

(where $M^I$ is at least one selected from the group consisting of Pb and Cu; $M^{II}$ is at least one selected from the group consisting of Li, Na, K, Rb, Cs, Au, and Ag; $M^{III}$ is at least one selected from the group consisting of Be, Mg, Ca, Sr, Ba, Zn, Cd, and Mn; $M^{IV}$ is at least one selected from the group consisting of Bi, Sn, Sb, Sc, Y, La, In, Ce, Pr, Nd, Pm, Sm, Eu, Gd, Tb, Dy, Ho, Er, Tm, Yb, and Lu; X is at least one selected from the group consisting of F; Cl, Br, and I; and a, b, c, d, e, f, g, h, x, and y are respectively set in the ranges of: $0 < a \leq 4$, $0 \leq b \leq 2$, $0 \leq c \leq 2$, $0 \leq d \leq 1$, $0 \leq e \leq 1$, $0 \leq f \leq 1$, $0 \leq g \leq 1$, $0 < h \leq 0.5$, $1 \leq x \leq 2$, and $1 \leq y \leq 5$)

The first or second light emitting part may comprise a phosphor represented by the following Chemical Formula 3:

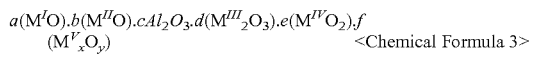

$a(M^I O).b(M^{II} O).c Al_2 O_3.d(M^{III}_2 O_3).e(M^{IV} O_2).f(M^V_x O_y)$ <Chemical Formula 3>

(where $M^I$ is at least one selected from the group consisting of Pb and Cu; $M^{II}$ is at least one selected from the group consisting of Be, Mg, Ca, Sr, Ba, Zn, Cd, and Mn; $M^{III}$ is at least one selected from the group consisting of B, Ga, and In; $M^{IV}$ is at least one selected from the group consisting of Si, Ge, Ti, Zr, and Hf; $M^V$ is at least one selected from the group consisting of Bi, Sn, Sb, Sc, Y, La, Ce, Pr, Nd, Pm, Sm, Eu, Gd, Tb, Dy, Ho, Er, Tm, Yb, and Lu; and a, b, c, d, e, f, x, and y are respectively set in the ranges of: $0 < a \leq 1$, $0 \leq b \leq 2$, $0 < c \leq 8$, $0 \leq d \leq 1$, $0 \leq e \leq 1$, $0 \leq f \leq 2$, $1 \leq x \leq 2$, and $1 \leq y \leq 5$)

The first or second light emitting part may comprise a phosphor represented by the following Chemical Formula 4:

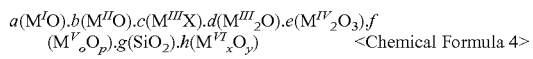

$a(M^I O).b(M^{II} O).c(M^{III} X).d(M^{III}_2 O).e(M^{IV}_2 O_3).f(M^V_o O_p).g(SiO_2).h(M^{VI}_x O_y)$ <Chemical Formula 4>

(where $M^I$ is at least one selected from the group consisting of Pb and Cu; $M^{II}$ is at least one selected from the group consisting of Be, Mg, Ca, Sr, Ba, Zn, Cd, and Mn; $M^{III}$ is at least one selected from the group consisting of Li, Na, K, Rb, Cs, Au, and Ag; $M^{IV}$ is at least one selected from the group consisting of Al, Ga, In, and B; $M^V$ is at least one selected from the group consisting of Ge, V, Nb, Ta, W, Mo, Ti, Zr, Hf; and P; $M^{VI}$ is at least one selected from the group consisting of Bi, Sn, Sb, Sc, Y, La, Ce, Pr, Nd, Pm, Sm, Eu, Gd, Tb, Dy, Ho, Er, Tm, Yb, and Lu; X is at least one selected from the group consisting of F, Cl, Br, and I; and a, b, c, d, e, f, g, h, o, p, x, and y are respectively set in the ranges of: $0 < a \leq 2$, $0 < b \leq 8$, $0 \leq c \leq 4$, $0 \leq d \leq 2$, $0 \leq e \leq 2$, $0 \leq f \leq 2$, $0 \leq g \leq 10$, $0 \leq h \leq 5$, $1 \leq o \leq 2$, $1 \leq p \leq 5$, $1 \leq x \leq 2$, and $1 \leq y \leq 5$)

The first or second light emitting part may comprise a phosphor represented by the following Chemical Formula 5:

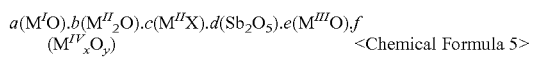

$a(M^I O).b(M^{II}_2 O).c(M^{II} X).d(Sb_2 O_5).e(M^{III} O).f(M^{IV}_x O_y)$ <Chemical Formula 5>

(where $M^I$ is at least one selected from the group consisting of Pb and Cu; $M^{II}$ is at least one selected from the group consisting of Li, Na, K, Rb, Cs, Au, and Ag; $M^{III}$ is at least one selected from the group consisting of Be, Mg, Ca, Sr, Ba, Zn, Cd, and Mn; $M^{IV}$ is at least one selected from the group consisting of Bi, Sn, Sc, Y. La, Pr, Sm, Eu, Tb, Dy, and Gd; X is at least one selected from the group consisting of F, Cl, Br, and I; and a, b, c, d, e, f, x, and y are respectively set in the ranges of: $0 < a \leq 2$, $0 \leq b \leq 2$, $0 \leq c \leq 4$, $0 < d \leq 8$, $0 \leq e \leq 8$, $0 \leq f \leq 2$, $1 \leq x \leq 2$, and $1 \leq y \leq 5$)

The first or second light emitting part may comprise a phosphor represented by the following Chemical Formula 6:

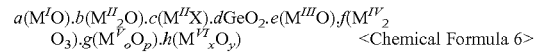

$a(M^I O).b(M^{II}_2 O).c(M^{II} X).dGeO_2.e(M^{III} O).f(M^{IV}_2 O_3).g(M^V_o O_p).h(M^{VI}_x O_y)$ <Chemical Formula 6>

(where $M^I$ is at least one selected from the group consisting of Pb and Cu; $M^{II}$ is at least one selected from the group consisting of Li, Na, K, Rb, Cs, Au, and Ag; $M^{III}$ is at least one selected from the group consisting of Be, Mg, Ca, Sr, Ba, Zn, and Cd; $M^{IV}$ is at least one selected from the group consisting of Sc, Y, B, Al, Ga, In, and La; $M^V$ is at least one selected from the group consisting of Si, Ti, Zr, Mn, V, Nb, Ta, W, and Mo; $M^{VI}$ is at least one selected from the group consisting of Bi, Sn, Pr, Sm, Eu, Gd, and Dy; X is at least one selected from the group consisting of F, Cl, Br, and I; and a, b, c, d, e, f, g, h, o, p, x, and y are respectively set in the ranges of: $0 < a \leq 2$, $0 \leq b \leq 2$, $0 \leq c \leq 10$, $0 < d \leq 10$, $0 \leq e \leq 14$, $0 \leq f \leq 14$, $0 \leq g \leq 10$, $0 \leq h \leq 2$, $1 \leq o \leq 2$, $1 \leq p \leq 5$, $1 \leq x \leq 2$, and $1 \leq y \leq 5$)

The first or second light emitting part may comprise a phosphor represented by the following Chemical Formula 7:

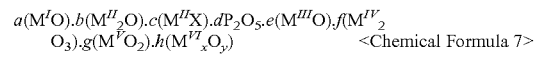

$a(M^I O).b(M^{II}_2 O).c(M^{II} X).dP_2 O_5.e(M^{III} O).f(M^{IV}_2 O_3).g(M^V_o O_p).h(M^{VI}_x O_y)$ <Chemical Formula 7>

(where $M^I$ is at least one selected from the group consisting of Pb and Cu; $M^{II}$ is at least one selected from the group consisting of Li, Na, K, Rb, Cs, Au, and Ag; $M^{III}$ is at least one selected from the group consisting of Be, Mg, Ca, Sr, Ba, Zn, Cd, and Mn; $M^{IV}$ is at least one selected from the group consisting of Sc, Y, B, Al, La, Ga, and In; $M^V$ is at least one selected from the group consisting of Si, Ge, Ti, Zr, Hf, V, Nb, Ta, W, and Mo; $M^{VI}$ is at least one selected from the group consisting of Bi, Sn, Pr, Sm, Eu, Gd, Dy, Ce, and Tb; X is at least one selected from the group consisting of F, Cl, Br, and I; and a, b, c, d, e, f, g, h, x, and y are respectively set in the ranges of: $0 < a \leq 2$, $0 \leq b \leq 12$, $0 \leq c \leq 16$, $0 < d \leq 3$, $0 \leq e \leq 5$, $0 \leq f \leq 3$, $0 \leq g \leq 2$, $0 \leq h \leq 2$, $1 \leq x \leq 2$, and $1 \leq y \leq 5$)

The first or second light emitting part may comprise a single or a plurality of phosphors.

Meanwhile, the fist and second LED chips may emit blue or UV light.

The light emitting device may further include a controller to control voltage applied to at least one of the first, second, and third light emitting parts. The controller may adjust the externally input voltage according to time, and particularly, may adjust the externally input voltage on a 24-hour cycle.

The first to third light emitting parts may be formed in a single package. The package may include a substrate upon which the first to third light emitting parts are mounted, and the phosphors of the first and second light emitting parts may be disposed above the first and second LED chips. Further, the package may further include a heat sink to dissipate heat generated from the LED chips, and the first to third LED chips may be disposed above the heat sink and the phosphors of the first and second light emitting parts may be disposed above the first and second LED chips.

The second light emitting part may be disposed nearer a center of the package than the first and third light emitting parts.

In the above description, although the first and second light emitting parts are divided based on a color temperature of 6000 K, the first and second light emitting parts may be divided based on a different color temperature. In accordance with another aspect of the present invention, a light emitting device includes a first light emitting part including a first LED chip and a first phosphor and emitting white light having a higher color temperature, a second light emitting part including a second LED chip and a second phosphor and emitting white light having a lower color temperature, and a third light emitting part including a third LED chip emitting light in the visible range of 580 nm or more. The second and third light emitting parts are operable independently of the first light emitting part, and realize a warm white color having a color temperature of 3000 K or less with the white light emitted from the second light emitting part and the light emitted from the third light emitting part. Accordingly, the light emitting device can realize white light having a variety of color temperatures. Meanwhile, a reference color temperature classifying the first and second light emitting parts may be in the range of 4000~6000 K.

DESCRIPTION OF THE DRAWINGS

The above and other features and advantages of the present invention will become apparent from the following description of exemplary embodiments given in conjunction with the accompanying drawings, in which.

DETAILED DESCRIPTION

Figure 1:
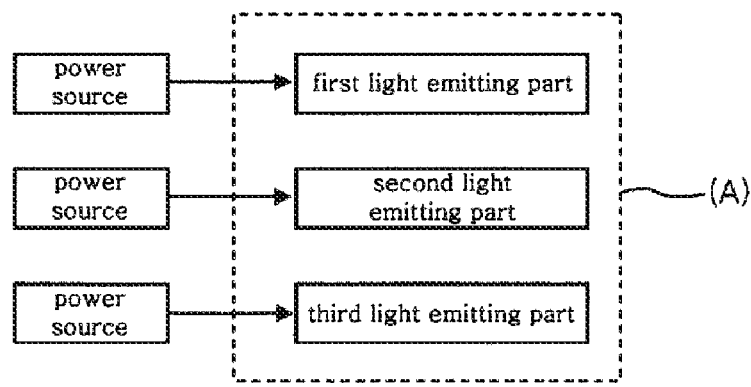
FIG. 1 is a block diagram illustrating a light emitting device according to one embodiment of the present invention.

Exemplary embodiments of the present invention are described in detail with reference to the accompanying drawings. It should be noted that the present invention is not limited to these embodiments and can be realized in various forms. The embodiments herein are given for the purpose of sufficient disclosure of the present invention and will help a person having ordinary knowledge in the art to gain a full understanding of the present invention. Like reference numerals will denote like components throughout the drawings.

According to the present invention, a light emitting device includes a first light emitting part emitting white light having a higher color temperature, a second light emitting part emitting white light having a lower color temperature, and a third light emitting part in a single package. The first light emitting part includes a first LED chip and a first phosphor, and emits white light, called daylight color, having a color temperature of 6000 K or more. The second light emitting part includes a second LED chip and a second phosphor, and emits white light having a color temperature less than 6000 K. The third light emitting part includes a third LED, which emits light in the visible range of 580 nm or more, so that the third light emitting part emits light in the visible range of 580 nm or more. The second and third light emitting parts are operable independently of the first light emitting part, and realize white light, called warm white color, with the white light emitted from the second light emitting part and the light emitted from the third light emitting part.

The first and second light emitting parts include the LED chips and the phosphors. Both LED chips may be an LED chip for emitting blue or UV light, which is mixed with light having undergone wavelength conversion through a predetermined phosphor, thereby realizing white light having desired spectrum and color temperature characteristics. The third light emitting part includes the LED chip that emits light in the visible range of 580 nm or more. Such an LED chip is made of, for example, (Al, In, Ga) P-based compound semiconductor, consumes less power, and emits visible light having a long wavelength. Accordingly, the light emitting device is capable of providing white light having a low color temperature by means of the second and third light emitting parts.

The LED chips and phosphors of the first and second light emitting parts can be constituted in various manners. For example, each of the first and second light emitting parts may include a single blue LED chip and a single yellow-emitting phosphor. In other words, white light can be obtained by mixing blue light emitted from the LED chips with yellow light having undergone wavelength conversion through the phosphors. Further, each of the first and second light emitting parts may include a single blue LED chip, a green-emitting phosphor, and an orange-emitting phosphor. As result, white light can be obtained by mixing blue light emitted from the LED chips with green light and orange light having undergone wavelength conversion through the phosphors. In this case, it is possible to obtain further improved color-rendering properties than the example in which the first and second light emitting parts include the blue LED chips and the yellow-emitting phosphors. As such, when employing the LED chips and the plural phosphors capable of emitting light in various light emission peaks, the light emitting device has improved color rendering properties. When using the plurality of phosphors, it is possible to obtain white light having a variety of color temperatures and color rendering properties according to the composition of each phosphor and the content ratio of the plural phosphors.

The phosphors include materials having various ranges of light emission peaks. For example, silicate-based phosphors having light emission peaks in the range from green to blue light are used as the phosphors. Hence, light emitted from the LED chips is used as an excitation source to realize various colors, thereby providing white light having various spectra and color temperature characteristics. Further, when the light emitting device includes a plurality of phosphors, the phosphors are selected from the same series materials, thereby minimizing interaction between the phosphors.

Examples of the phosphors include aluminate-based phosphors, silicate-based phosphors, oxynitride-based phosphors, antimonite-based phosphors, germanate-based phosphors, and phosphate-based phosphors. In particular, phosphors containing lead or copper can provide high stability and excellent light excitation properties.

The aluminate-based phosphors may include phosphors represented by Chemical Formulas 1, 2 and 3 as follows.

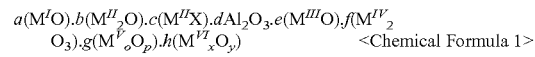   <Chemical Formula 1>

In Chemical Formula 1, $M^I$ is at least one selected from the group consisting of Pb and Cu; $M^{II}$ is at least one selected from the group consisting of Li, Na, K, Rb, Cs, Au, and Ag; $M^{III}$ is at least one selected from the group consisting of Be, Mg, Ca, Sr, Ba, Zn, Cd, and Mn; $M^{IV}$ is at least one selected from the group consisting of Sc, B, Ga, and In; $M^V$ is at least one selected from the group consisting of Si, Ge, Ti, Zr, Mn, V, Nb, Ta, W, and Mo; $M^{VI}$ is at least one selected from the group consisting of Bi, Sn, Sb, Sc, Y, La, Ce, Pr, Nd, Pm, Sm, Eu, Gd, Tb, Dy, Ho, Er, Tm, Yb, and Lu; and X is at least one selected from the group consisting of F, Cl, Br, and I.

Further, in Chemical Formula 1, a, b, c, d, e, f, g, h, o, p, x, and y are respectively set in the ranges of: $0<a\leq2$, $0\leq b\leq2$, $0\leq c\leq2$, $0\leq d\leq8$, $0\leq e\leq4$, $0\leq f\leq3$, $0\leq g\leq8$, $1\leq o\leq2$, $1\leq p\leq5$, $0\leq h\leq2$, $1\leq x\leq2$, and $1\leq y\leq5$.

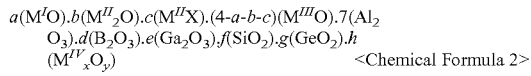
<Chemical Formula 2>

In Chemical Formula 2, $M^I$ is at least one selected from the group consisting of Pb and Cu; $M^{II}$ is at least one selected from the group consisting of Li, Na, K, Rb, Cs, Au, and Ag; $M^{III}$ is at least one selected from the group consisting of Be, Mg, Ca, Sr, Ba, Zn, Cd, and Mn; $M^{IV}$ is at least one selected from the group consisting of Bi, Sn, Sb, Sc, Y, La, In, Ce, Pr, Nd, Pm, Sm, Eu, Gd, Tb, Dy, Ho, Er, Tm, Yb, and Lu; and X is at least one selected from the group consisting of F, Cl, Br, and I.

Further, in Chemical Formula 2, a, b, c, d, e, f, g, h, x, and y are respectively set in the ranges of: $0<a\leq4$, $0\leq b\leq2$, $0\leq c\leq2$, $0\leq d\leq1$, $0\leq e\leq1$, $0\leq f\leq1$, $0\leq g\leq1$, $0<h\leq0.5$, $1\leq x\leq2$, and $1\leq y\leq5$.

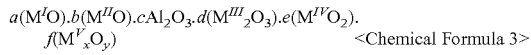
<Chemical Formula 3>

In Chemical Formula 3, $M^I$ is at least one selected from the group consisting of Pb and Cu; $M^{II}$ is at least one selected from the group consisting of Be, Mg, Ca, Sr, Ba, Zn, Cd, and Mn; $M^{III}$ is at least one selected from the group consisting of B, Ga, and In; $M^{IV}$ is at least one selected from the group consisting of Si, Ge, Ti, Zr, and Hf; and $M^V$ is at least one selected from the group consisting of Bi, Sn, Sb, Sc, Y, La, Ce, Pr, Nd, Pm, Sm, Eu, Gd, Tb, Dy, Ho, Er, Tm, Yb, and Lu.

Further, in Chemical Formula 3, a, b, c, d, e, f, x, and y are respectively set in the ranges of: $0<a\leq1$, $0\leq b\leq2$, $0<c\leq8$, $0\leq d\leq1$, $0\leq e\leq1$, $0<f\leq2$, $1\leq x\leq2$, and $1\leq y\leq5$.

The silicate-based phosphors may include phosphors represented by the following Chemical Formula 4.

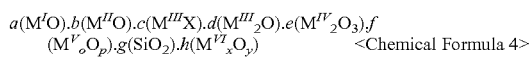
<Chemical Formula 4>

In Chemical Formula 4, $M^I$ is at least one selected from the group consisting of Pb and Cu; $M^{II}$ is at least one selected from the group consisting of Be, Mg, Ca, Sr, Ba, Zn, Cd, and Mn; $M^{III}$ is at least one selected from the group consisting of Li, Na, K, Rb, Cs, Au, and Ag; $M^{IV}$ is at least one selected from the group consisting of Al, Ga, In, and B; $M^V$ is at least one selected from the group consisting of Ge, V, Nb, Ta, W, Mo, Ti, Zr, Hf, and P; $M^{VI}$ is at least one selected from the group consisting of Bi, Sn, Sb, Sc, Y, La, Ce, Pr, Nd, Pm, Sm, Eu, Gd, Tb, Dy, Ho, Er, Tm, Yb, and Lu; and X is at least one selected from the group consisting of F, Cl, Br, and I.

Further, in Chemical Formula 4, a, b, c, d, e, f, g, h, o, p, x, and y are respectively set in the ranges of: $0<a\leq2$, $0\leq b\leq8$, $0\leq c\leq4$, $0\leq d\leq2$, $0\leq e\leq2$, $0\leq f\leq2$, $0\leq g\leq10$, $0\leq h\leq5$, $1\leq o\leq2$, $1\leq p\leq5$, $1\leq x\leq2$, and $1\leq y\leq5$.

The antimonite-based phosphors may include phosphors represented by the following Chemical Formula 5.

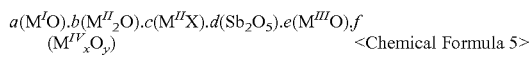
<Chemical Formula 5>

In Chemical Formula 5, $M^I$ is at least one selected from the group consisting of Pb and Cu; $M^{II}$ is at least one selected from the group consisting of Li, Na, K, Rb, Cs, Au, and Ag; $M^{III}$ is at least one selected from the group consisting of Be, Mg, Ca, Sr, Ba, Zn, Cd, and Mn; $M^{IV}$ is at least one selected from the group consisting of Bi, Sn, Sc, Y, La, Pr, Sm, Eu, Tb, Dy, and Gd; and X is at least one selected from the group consisting of F, Cl, Br, and I.

Further, in Chemical Formula 5, a, b, c, d, e, f, x, and y are respectively set in the ranges of: $0<a\leq2$, $0\leq b\leq2$, $0\leq c\leq4$, $0<d\leq8$, $0\leq e\leq8$, $0\leq f\leq2$, $1\leq x\leq2$, and $1\leq y\leq5$.

The germanate-based phosphors may include phosphors represented by the following Chemical Formula 6.

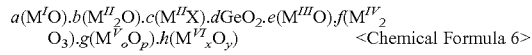
<Chemical Formula 6>

In Chemical Formula 6, $M^I$ is at least one selected from the group consisting of Pb and Cu; $M^{II}$ is at least one selected from the group consisting of Li, Na, K, Rb, Cs, Au, and Ag; $M^{III}$ is at least one selected from the group consisting of Be, Mg, Ca, Sr, Ba, Zn, and Cd; $M^{IV}$ is at least one selected from the group consisting of Sc, Y, B, Al, Ga, In, and La; $M^V$ is at least one selected from the group consisting of Si, Ti, Zr, Mn, V, Nb, Ta, W, and Mo; $M^{VI}$ is at least one selected from the group consisting of Bi, Sn, Pr, Sm, Eu, Gd, and Dy; and X is at least one selected from the group consisting of F, Cl, Br, and I.

Further, in Chemical Formula 6, a, b, c, d, e, f, g, h, o, p, x, and y are respectively set in the ranges of: $0<a\leq2$, $0\leq b\leq2$, $0\leq c\leq10$, $0<d\leq10$, $0\leq e\leq14$, $0\leq f\leq14$, $0\leq g\leq10$, $0\leq h\leq2$, $1\leq o\leq2$, $1\leq p\leq5$, $1\leq x\leq2$, and $1\leq y\leq5$.

The phosphate-based phosphors may include phosphors represented by the following Chemical Formula 7.

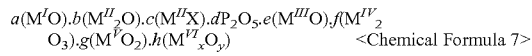
<Chemical Formula 7>

In Chemical Formula 7, $M^I$ is at least one selected from the group consisting of Pb and Cu; $M^{II}$ is at least one selected from the group consisting of Li, Na, K, Rb, Cs, Au, and Ag; $M^{III}$ is at least one selected from the group consisting of Be, Mg, Ca, Sr, Ba, Zn, Cd, and Mn; $M^{IV}$ is at least one selected from the group consisting of Sc, Y, B, Al, La, Ga, and In; $M^V$ is at least one selected from the group consisting of Si, Ge, Ti, Zr, Hf, V, Nb, Ta, W, and Mo; $M^{VI}$ is at least one selected from the group consisting of Bi, Sn, Pr, Sm, Eu, Gd, Dy, Ce, and Tb; and X is at least one selected from the group consisting of F, Cl, Br, and I.

Further, in Chemical Formula 7, a, b, c, d, e, f, g, h, x, and y are respectively set in the ranges of: $0<a\leq2$, $0\leq b\leq12$, $0\leq c\leq16$, $0<d\leq3$, $0\leq e\leq5$, $0\leq f\leq3$, $0\leq g\leq2$, $0\leq h\leq2$, $1\leq x\leq2$, and $1\leq y\leq5$.

FIG. 1 is a block diagram illustrating a light emitting device according to one embodiment of the present invention.

Referring to FIG. 1, the light emitting device includes a first light emitting part emitting a daylight color having a color temperature of 6000 K or more, a second light emitting part emitting white light having a color temperature less than 6000 K, and a third light emitting part emitting light in the visible range of 580 nm or more. The second and third light emitting parts are operable independently of the first light emitting part, and realize white light, called warm white, having a color temperature of 3000 K or less.

In the light emitting device, since each of the plural light emitting parts is electrically connected in a single package (A), it is possible to independently operate the first to third light emitting parts. For example, when power is applied only to the first light emitting part, it is possible to realize white light having a color temperature of 6000 K or more, that is, daylight color. Further, when power is applied only to the second light emitting part, it is possible to realize white light having a color temperature less than 6000 K, and, when power is applied only to the third light emitting part, it is possible to realize white light having a color temperature of 3000K or less, that is, warm white.

As such, it is possible to realize the white light having a color temperature of 3000 K or less with the LED chips and the red-based phosphor. However, since the red-based phosphor has lower luminescence efficiency, it is necessary to rapidly increase an amount of phosphor and driving power in order to decrease the color temperature. As a result, power consumption of the light emitting device increases rapidly. However, since a phosphate-based LED chip has a high light emitting efficiency and emits visible light having a long wavelength, it is possible to realize white light of a lower color temperature with low power by using such an LED chip.

Meanwhile, it is possible to realize white light having a variety of spectra and color temperatures in a wide range by applying power only to the first and second light emitting parts or by simultaneously applying power to the first to third light emitting parts.

As such, since the light emitting device of the present invention can realize white light having such various spectra and color temperatures, even a single package of the light emitting device can be applied in various manners suitable for desired moods and applications. For example, at the daytime, only the first light emitting part of the light emitting device is operated to improve brain activity and concentration of a user with white light of a daylight color temperature of 6000 K or more, whereas at the night, the second and third light emitting parts are operated to allow the user to relax with white light of a warm white color temperature of 3000 K or less. In particular, the light emitting device is controlled to emit light having a suitable wavelength or a suitable color temperature depending on the circadian rhythm of humans, thereby enabling improvement of the user's health.

Figure 2:
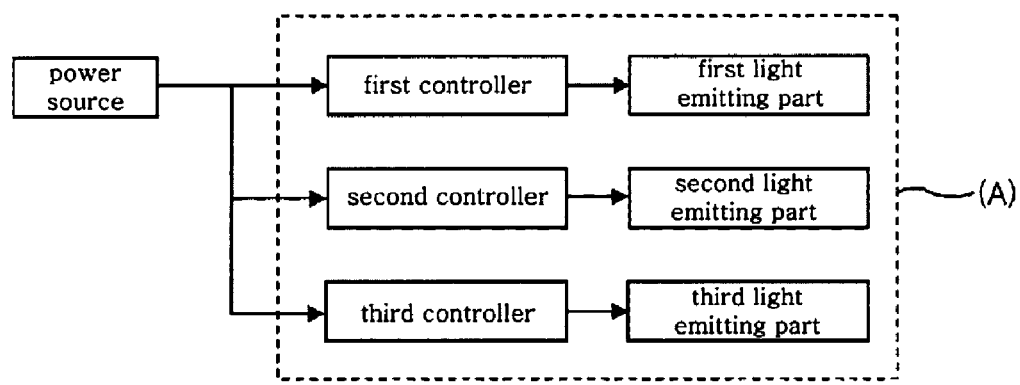
FIG. 2 is a block diagram illustrating a light emitting device according to another embodiment of the present invention.

FIG. 2 is a block diagram illustrating a light emitting device according to another embodiment of the present invention.

Referring to FIG. 2, the light emitting device of this embodiment includes a first light emitting part emitting a daylight color having a color temperature of 6000 K or more, a second light emitting part emitting white light having a color temperature less than 6000 K, and a third light emitting part emitting light in a visible range of 580 nm or more. The light emitting device further includes a first controller connected to the first light emitting part, a second controller connected to the second light emitting part, and a third controller connected to the third light emitting part. The first to third controllers control voltage to be applied to the first to third light emitting parts.

The first to third controllers adjust and output voltage input from an external power source based on time of day when controlling the voltage to be applied to the first to third light emitting parts. For this purpose, each of the first to third controllers may include a timer and a voltage controller circuit. In other words, when voltage is input from the external power source, the controllers adjust the voltage according to the time of day through the timer and the voltage controller circuits, and supply the adjusted voltage to the first to third light emitting parts.

Figure 3A:
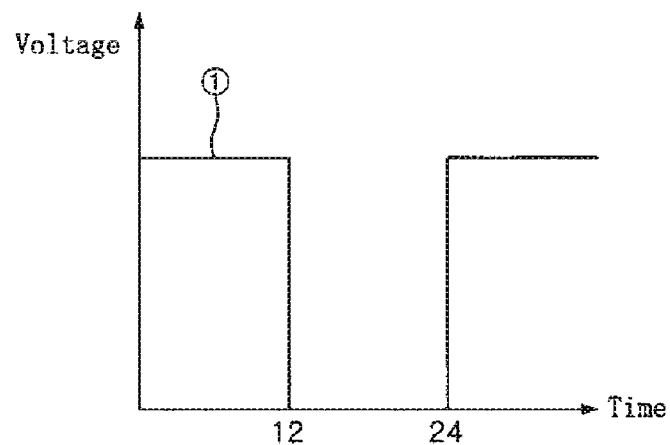
FIGS. 3a and 3b are graphs depicting one embodiment of first to third controllers of the light emitting device.
Figure 3B:
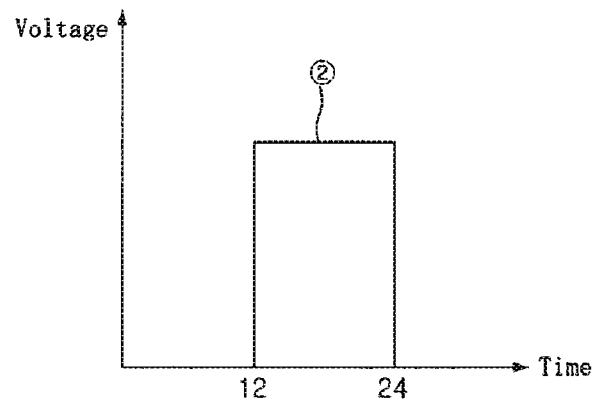

FIGS. 3a and 3b are graphs depicting one example of the first to third controllers. In FIGS. 3a and 3, the first controller (①) allows voltage from the external power source to be transferred unaltered to the light emitting part for 12 hours and then shuts off the voltage for the next 12 hours, as shown in FIG. 3a. On the contrary, the second controller (②) prevents voltage from the external power source from being applied to the light emitting part for 12 hours and then allows the voltage to be transferred unaltered thereto for the next 12 hours, as shown in FIG. 3b. The third controller may transfer the voltage from the external voltage source to the light emitting part in an unaltered state during the same period of time as that of the second controller. In other words, the third controller transfers the voltage from the external voltage source in the unaltered state for 12 hours a day to drive only the first light emitting part, and transfers the voltage in the unaltered state for the next 12 hours to drive only the second and third light emitting parts.

Operation of the light emitting device will be described in the following. When external power is applied to the first to third controllers, the first to third controllers adjust their respective voltages according to the time and apply the adjusted voltages to the first to third light emitting parts. As described above, when operating the light emitting parts, voltage applied from the external power source is transferred only to the first light emitting part without adjustment for 12 hours a day, and is then transferred only to the second and third light emitting parts without adjustment for the next 12 hours. Thus, for 12 hours a day, for example, during the daytime, only the first light emitting part of the light emitting device is operated to realize white light having a daylight color temperature of 6000 K or more, and during the next 12 hours, for example, the night, only the second and third light emitting parts are operated to realize white light having a warm white color temperature of 3000 K or less.

Figure 4A:
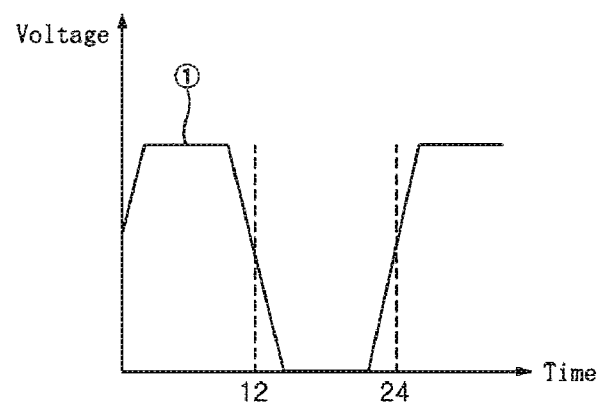
FIGS. 4a and 4b are graphs depicting another embodiment of first to third controllers of the light emitting device.
Figure 4B:
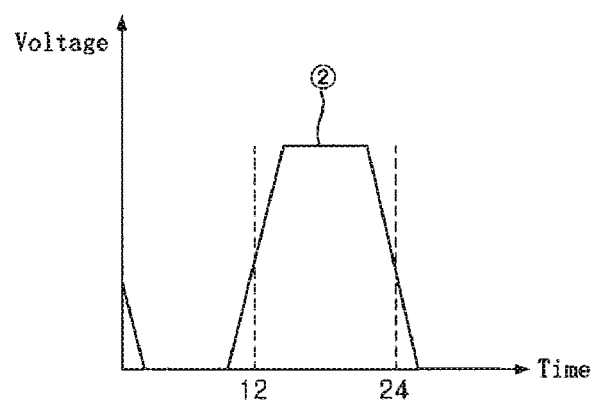

In the above description, power-On/Off with respect to the first to third light emitting parts is illustrated as one example, but the present invention is not limited thereto. For example, as shown in FIGS. 4a and 4b, the controllers may be configured to increase or decrease voltage according to time so as to increase or decrease intensity of light emitted from the first to third light emitting parts. Hence, the light emitting device can be adjusted to increase or decrease the color temperature of white light emitted therefrom.

As such, since operation of the first to third light emitting parts can be controlled by means of the first to third controllers, the light emitting device can be applied in various manners as needed. That is, it is possible to manufacture a light emitting device capable of automatically adjusting the color temperature according to time without a separate input operation. For example, it is possible to manufacture a light emitting device capable of emitting white light having a higher color temperature during the daytime while emitting white light having a lower color temperature during the night, as described above. In particular, the light emitting device is controlled to emit light having a suitable wavelength or a suitable color temperature depending on the circadian rhythm of humans, thereby enabling improvement of the user's health.

In the above example, the controller is capable of adjusting the voltage according to time, but the present invention is not limited thereto. Instead, the controller may further include a separate input section to adjust the color temperature as needed by a user. Further, although external power is simultaneously applied to the first to third controllers in the above example, the present invention is not limited thereto. For example, the first to third controllers may be connected to separate external power sources to be independently operated. Alternatively, a single controller can be used to control the second and third light emitting parts to be operated during the same period of time, or can be used to control each of the first to third light emitting parts to be operated independently. Further, the second and third light emitting parts are described as being operated at the same time, but the present invention is not limited thereto. That is, a separate period of time for operating only the second or third light emitting part can be provided in addition to the time period for which the second and third light emitting parts are operated at the same time.

As such, since the light emitting device of the present invention can realize white light of various spectra and color temperatures, even a single package (A) of the light emitting device can be applied in various manners suitable for desired moods and applications. For example, at the daytime, only the first light emitting part of the light emitting device is operated to improve brain activity and concentration of a user with white light of a daylight color temperature of 6000 K or more, whereas at the night, the second and third light emitting parts are operated to allow the user to relax with white light of a warm white color temperature of 3000 K or less. In particular, the light emitting device is controlled to emit light having a suitable wavelength or a suitable color temperature depending on the circadian rhythm of humans, thereby enabling improvement of the user's health.

Further, instead of constituting light emitting parts in separate packages for realizing white light of various spectra and color temperatures as in the conventional technique, the present invention constitutes the light emitting parts in a single package, thereby simplifying a manufacturing process and reducing manufacturing costs while increasing space efficiency.

The present invention will be described in more detail with reference to embodiments as follows.

EXAMPLE 1

A first light emitting part is constituted with an LED chip emitting blue light of 456 nm, $Cu_{0.15}Ba_{1.82}Sr_{0.03}Si_{0.99}Ge_{0.01}O_4$:Eu phosphor having a light emission peak of 515 nm, and $Cu_{0.05}Sr_{1.72}Ca_{0.23}Si_{0.99}Ge_{0.01}O_4$:Eu phosphor having a light emission peak of 593 nm.

A second light emitting part is constituted with an LED chip emitting blue light of 456 nm, $Cu_{0.05}Ba_{1.84}Sr_{0.01}Si_{0.99}Zr_{0.01}O_4$:Eu phosphor having a light emission peak of 508 nm, and $Cu_{0.05}Sr_{1.85}Ca_{0.10}SiO_4$:Eu phosphor having a light emission peak of 605 nm. Additionally, a third light emitting part is constituted with an LED chip emitting light in a visible range of 580 nm or more.

Figure 5:
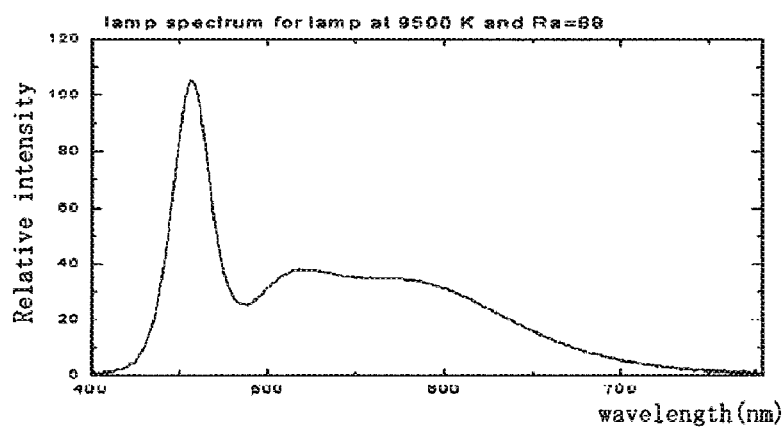
FIGS. 5 and 6 are diagrams showing emission spectrums of Example 1 according to the present invention.
Figure 6:
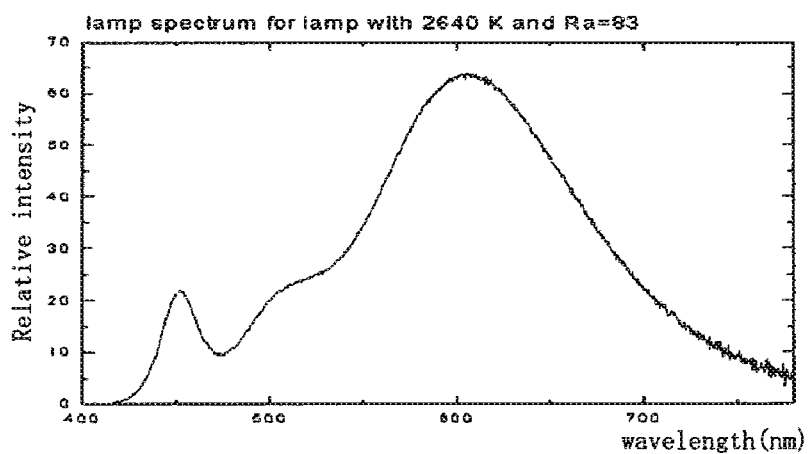

FIG. 5 is a diagram showing an emission spectrum of the first light emitting part, and FIG. 6 is a diagram showing an emission spectrum of the second light emitting part. As can be seen from these figures, the first light emitting part exhibits a higher intensity of light in the blue emitting region, and the second light emitting part exhibits a higher intensity of light in the yellow and red emitting regions. In other words, it can be understood that the first light emitting part has a higher color temperature, whereas the second light emitting part has a lower color temperature.

In this example, the first light emitting part realizes white light having a color temperature of 9500 K and an excellent color-rendering property with a color-rendering index of 88. Further, the second light emitting part realizes white light having a color temperature of 2640 K and an excellent color-rendering property with a color-rendering index of 83.

By selectively operating the first and second light emitting parts, it is possible to realize white light having excellent color rendering properties, and various spectra and color temperatures. For example, at the daytime, only the first light emitting part of the light emitting device is operated to realize white light having a higher color temperature of 9500 K, whereas at the night, only the second light emitting part is operated to realize white light having a lower color temperature of 2640 K. In addition, with the third light emitting part that includes the LED chip emitting light in the visible range of 580 nm or more, it is possible to realize white light having a much lower color temperature than 2640 K.

EXAMPLE 2

A first light emitting part is constituted with an LED chip emitting blue light of 456 nm, $Cu_{0.15}Ba_{1.82}Sr_{0.03}Si_{0.99}Ge_{0.01}O_4$:Eu phosphor having a light emission peak of 515 nm, and $Cu_{0.05}Sr_{1.8}Ca_{0.15}SiO_4$:Eu phosphor having a light emission peak of 600 nm.

A second light emitting part is constituted with an LED chip emitting blue light of 456 nm, $Cu_{0.15}Ba_{1.82}Sr_{0.03}Si_{0.99}Ge_{0.01}O_4$:Eu phosphor having a light emission peak of 515 nm, and $Cu_{0.05}Sr_{1.8}Ca_{0.15}SiO_4$:Eu phosphor having a light emission peak of 600 nm. Additionally, a third light emitting part is constituted with an LED chip emitting light in the visible range of 580 nm or more.

In this embodiment, the first and second light emitting parts can realizes white light having different color temperatures and color rendering properties with two phosphors of different composition.

Figure 7:
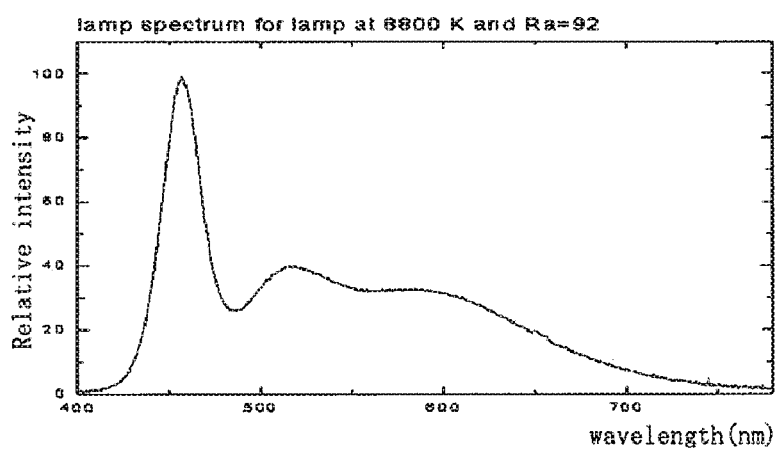
FIGS. 7 and 8 are diagrams showing emission spectrums of Example 2 according to the present invention.
Figure 8:
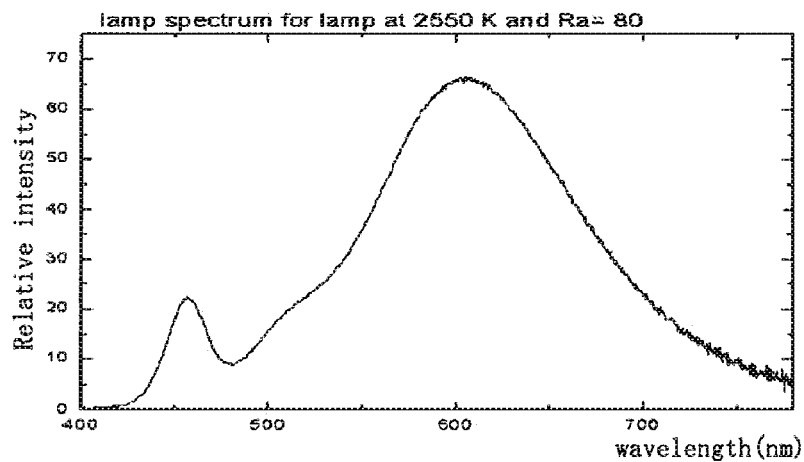

FIG. 7 is a diagram showing an emission spectrum of the first light emitting part, and FIG. 8 is a diagram showing an emission spectrum of the second light emitting part. As can be seen from these figures, the first light emitting part has a higher color temperature, and the second light emitting part has a lower color temperature.

In this example, the first light emitting part realizes white light having a color temperature of 8800 K and an excellent color-rendering property with a color-rendering index of 92. Further, the second light emitting part realizes white light having a color temperature of 2550 K and an excellent color-rendering property with a color-rendering index of 80.

By selectively operating the first and second light emitting parts, it is possible to realize white light having excellent color rendering properties, and various spectra and color temperatures. For example, at the daytime, only the first light emitting part of the light emitting device is operated to realize white light having a higher color temperature of 8800 K, whereas at the night, only the second light emitting part is operated to realize white light having a lower color temperature of 2550 K. In addition, by simultaneously operating the second and third light emitting parts, it is possible to realize white light having a much lower color temperature than 2550 K.

EXAMPLE 3

A first light emitting part is constituted with an LED chip emitting UV light of 405 nm, $Cu_{0.02}Ba_{2.8}Sr_{0.2}Mg_{0.98}Si_2O_8$:Eu phosphor having a light emission peak of 440 nm, $Cu_{0.15}Ba_{1.84}Sr_{0.01}Si_{0.99}Zr_{0.01}O_4$:Eu phosphor having a light emission peak of 508 nm, $Cu_{0.02}Ba_{0.98}Sr_{0.98}Ca_{0.02}SiO_4$:Eu phosphor having a light emission peak of 565 nm, and $Cu_{0.15}Mg_{0.85}BaP_2O_7$:Eu, Mn phosphor having a light emission peak of 630 nm.

A second light emitting part is constituted with an LED chip emitting UV light of 405 nm, $Cu_{0.02}Ba_{2.8}Sr_{0.2}Mg_{0.98}Si_2O_8$:Eu phosphor having a light emission peak of 440 nm, $Cu_{0.15}Ba_{0.82}Sr_{0.03}Si_{0.99}Ge_{0.01}O_4$:Eu phosphor having a light emission peak of 515 nm, $Cu_{0.05}Sr_{1.72}Ca_{0.23}Si_{0.99}Ge_{0.01}O_4$:Eu phosphor having a light emission peak of 593 nm, $Cu_{0.15}Mg_{0.85}BaP_2O_7$:Eu, Mn phosphor having a light emission peak of 630 nm. Additionally, a third light emitting part is constituted with an LED chip emitting light in the visible range of 580 nm or more.

Figure 9:
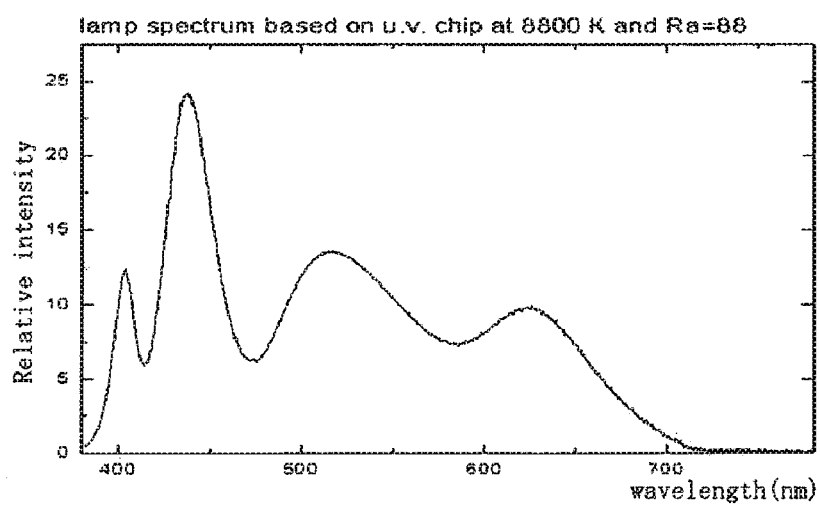
FIGS. 9 and 10 are diagrams showing emission spectrums of Example 3 according to the present invention.
Figure 10:
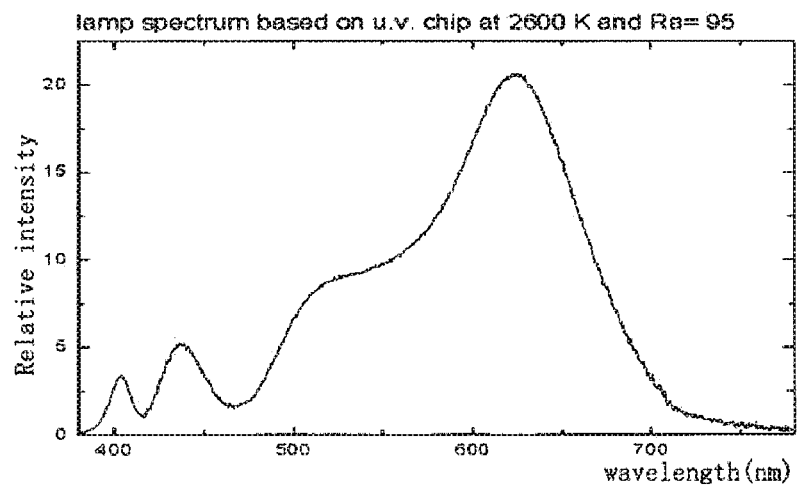

FIG. 9 is a diagram showing an emission spectrum of the first light emitting part, and FIG. 8 is a diagram showing an emission spectrum of the second light emitting part. As can be seen from these figures, the first light emitting part has a higher color temperature, and the second light emitting part has a lower color temperature.

In this example, the first light emitting part realizes white light having a color temperature of 8800 K and an excellent color-rendering property with a color-rendering index of 88. Further, the second light emitting part realizes white light having a color temperature of 2600 K and an excellent color-rendering property with a color-rendering index of 95.

By selectively operating the first and second light emitting parts, it is possible to realize white light having excellent color rendering properties, and various spectra and color temperatures. For example, at the daytime, only the first light emitting part of the light emitting device is operated to realize white light having a higher color temperature of 8800 K, whereas at the night, only the second light emitting part is operated to realize white light having a lower color temperature of 2600 K. In addition, by simultaneously operating the second and third light emitting parts, it is possible to realize white light having a much lower color temperature than 2600 K.

In these examples, the second light emitting part is constituted to provide white light having a color temperature of 3000 K or less. However, the present invention is not limited thereto, and the second light emitting part may be constituted to realize white light having a color temperature of 3000~6000 K by reducing an amount of red-based phosphor in the second light emitting part. Alternatively, the second and third light emitting parts may be constituted to realize white light having a color temperature of 3000 K or less while being operated at the same time. In this case, it is possible to reduce power consumption using the third light emitting part having high emission efficiency while reducing the amount of red-based phosphor having lower emission efficiency in the second light emitting part.

FIGS. 11 to 15 are views of examples in which the light emitting device of the present invention is applied to various structures.

Figure 11:
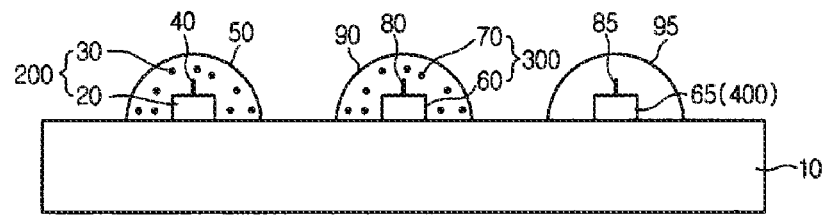
FIGS. 11 to 16 are schematic cross-sectional views of embodiments in which the light emitting device is applied to various structures according to the present invention.

Referring to FIG. 11, a light emitting device includes a substrate 10, and first to third light emitting parts 200, 300, and 400 formed on the substrate 10.

The first light emitting part 200 includes a first LED chip 20 and a first phosphor 30 which is dotted as a mixture with a curable resin 50, for example, epoxy or silicone, on the first LED chip 20. A bonding wire 40 may be bonded on the first LED chip 20. The first light emitting part 200 realizes white light having a daylight color temperature of 6000 K or more by mixing light emitted from the first LED chip 20 with light having undergone wavelength conversion through the first phosphor 30.

Similarly, the second light emitting part 300 includes a second LED chip 60 and a second phosphor 70 which is dotted as a mixture with a curable resin 90 on the second LED chip 60. Further, a bonding wire 80 may be bonded on the second LED chip 60. The second light emitting part 300 realizes white light having a warm white color temperature less than 6000 K by mixing light emitted from the second LED chip 60 with light having undergone wavelength conversion through the second phosphor 70.

The third light emitting part 400 includes a third LED chip 65. The third LED chip 65 is dotted and sealed with a curable resin 95. Further, a bonding wire 85 may be bonded on the third LED chip 65. The third LED chip 65 emits light in the visible range of 580 nm or more.

Figure 12:
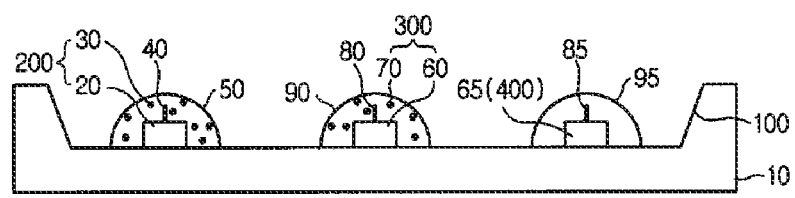

The substrate 10 may have a predetermined recess formed thereon where the first to third light emitting parts 200, 300 and 400 are formed. A lateral side of the recess 100 may have a predetermined slope. Referring to FIG. 12, the light emitting device includes the substrate 10, on which the recess 100 is formed, and the first, second and third light emitting parts 200, 300 and 400, which are formed on a bottom surface of the recess 100. Specifically, the first light emitting part 200 including the first LED chip 20 and the first phosphor 30, the second light emitting part 300 including the second LED chip 60 and the second phosphor 70, and the third light emitting part 400 including the third LED chip 65 are formed on the bottom surface of the recess 100. Further, the curable resin 50 mixed with the first phosphor 30, the curable resin 90 mixed with the second phosphor 70, and the curable resin 95 are respectively formed on the first to third LED chips 20, 60 and 65 by dotting. In the recess 100, the lateral side having a predetermined slope serves to maximize reflection and emission efficiency of light emitted from the LED chips 20, 60 and 65. Although not shown in the drawings, the light emitting device may further include a molding part, which is formed by filling the recess 100 with a transparent curable resin, in order to protect the first, second and third light emitting parts 200, 300 and 400. Meanwhile, since the second light emitting part 200 includes the phosphor having lower luminescence efficiency, the second light emitting part 200 may be located further distant from the lateral side of the recess 100 than the first and third light emitting parts to ensure emission intensity of the second light emitting part 200. Accordingly, the second light emitting part 300 is preferably disposed between the first and third light emitting parts.

Figure 13:
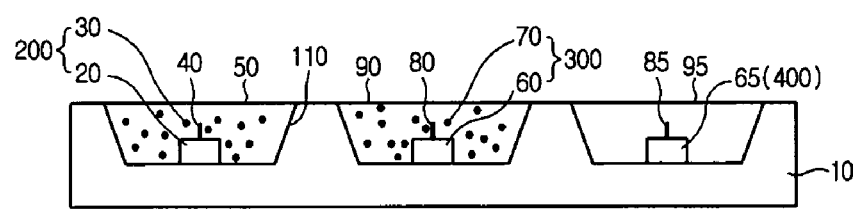

Alternatively, the light emitting device may include a recess so as to corresponding to each of the first to third light emitting parts 200, 300 and 400. Referring to FIG. 13, the light emitting device includes the substrate 10, which has a plurality of recesses 110 formed to separate the first, second, and third light emitting parts 200, 300 and 400, and the first, second, and third light emitting parts 200, 300 and 400 which are separately formed on bottom surfaces of the recesses 110, respectively. Specifically, the first LED chip 20 is mounted on the bottom surface of one recess 110, and the recess 110 is filled with a mixture 50 of the first phosphor 30 and the curable resin, thereby forming the first light emitting part 300. The second light emitting part 300 may also be formed in this manner. Further, after the third LED chip 65 is mounted on another recess 110, the recess 110 may be filled with the curable resin. At this time, each of the recess has a predetermined slope on a lateral side to maximize reflection and emission efficiency of light emitted from the LED chips 20, 60 and 65.

Figure 14:
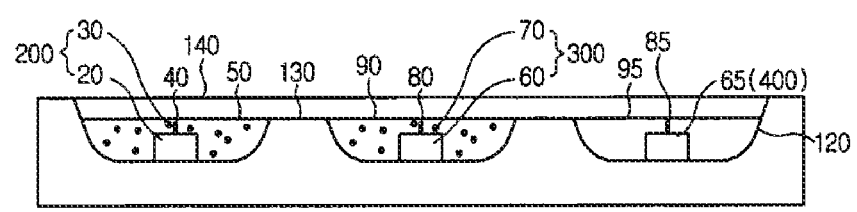

The lateral side of the recess may be formed into a round slope instead of a linear slop. Referring to FIG. 14, the light emitting device includes the substrate 10, which has a recess 120 having a lateral side of a round slope, and the first, second and third light emitting parts 200, 300 and 400 formed on an bottom surface of the recess 120. The light emitting device may further include a partition 130 to separate the first light emitting part 200 from the light emitting part 300. As in the case of FIG. 13, the partition 130 may have the same height as that of the substrate 10. Alternatively, as shown in FIG. 14, the partitions 130 may have a lower height than that of the substrate 10 to separate the first to third light emitting parts 200, 300 and 400 from one another, and a molding part 140 may be further formed on the substrate 10 to commonly encapsulate the first to third light emitting parts 200, 300 and 400. This provides advantages of protecting the first to third light emitting parts 200, 300 and 400 while facilitating mixture of light emitted therefrom. When the molding part 140 is formed to commonly encapsulate the first to third light emitting parts 200, 300 and 400, the curable resin 95 used for sealing the third LED chip 64 can be omitted.

Figure 15:
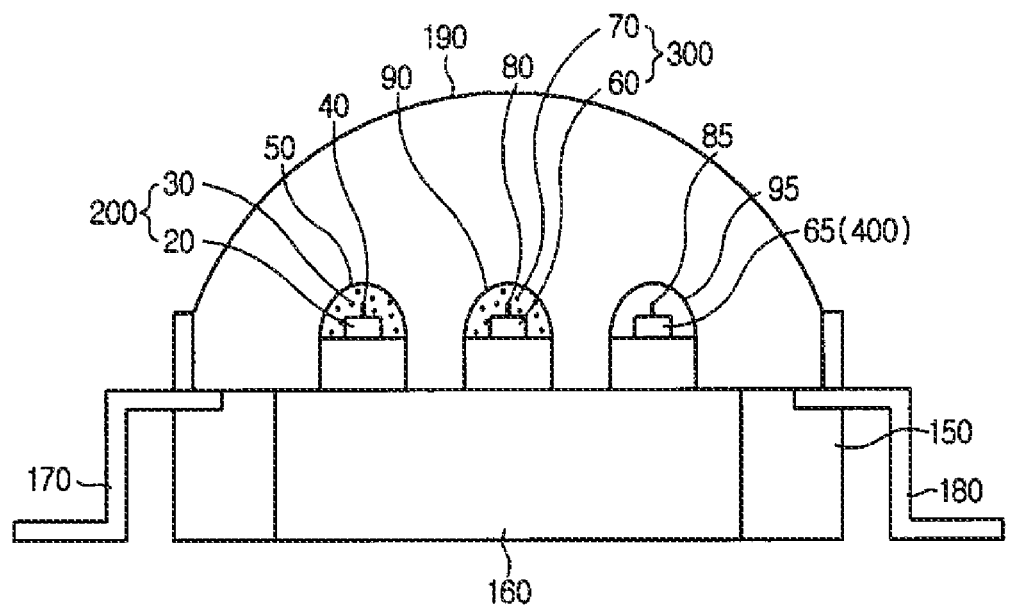

Referring to FIG. 15, another embodiment of the light emitting device, which has a heat dissipation structure for efficiently dissipating heat from the first to third LED chips 20, 60 and 65, is shown. The light emitting device includes a heat sink 160, and first to third light emitting parts 200, 300 and 400 disposed above the heat sink 160, a housing 150 surrounding the heat sink 160, lead frames 170 and 180 protruding from the housing 150 to supply external power, and a molding part 190 encapsulating the first to third light emitting parts 200, 300 and 400. The heat sink 160 may be formed of a material having excellent thermal conductivity, for example, metal, to allow more effective dissipation of heat from the LED chips 20, 60 and 65.

The heat sink 160 includes protrusions formed corresponding to the respective light emitting parts 200, 300 and 400 in order to allow the curable resins 50, 90 and 95 to be easily provided on the respective LED chips 20, 60 and 65 by dotting. Of course, the present invention is not limited to this configuration. Alternatively, the light emitting parts may be formed on a planar surface of the heat sink. Alternatively, the heat sink may include a predetermined recess such that the light emitting parts can be formed on an bottom surface of the recess.

In the above embodiments, the second and third light emitting parts are separated from each other. However, the second and third light emitting parts may be formed together in the same recess, and the curable resin comprising the second phosphor may be provided on the second and third light emitting parts 60 and 65 by dotting.

In the above description, the number of LED chips constituting each of the first to third light emitting parts is one. However, the present invention is not limited to a single LED chip for each light emitting part. Instead, each of the first to third light emitting parts may include a plurality of LED chips.

As such, the light emitting device of the invention can be applied to various products having different configurations, and can be applied to general lighting devices. For application of the light emitting device of the invention to the general lighting devices, it is necessary to have a number of LED chips, for example, 50~80 LED chips. For this purpose, packages having various configurations as described above may be mounted on the substrate. Alternatively, the plural LED chips may be directly mounted on the substrate.

Figure 16:
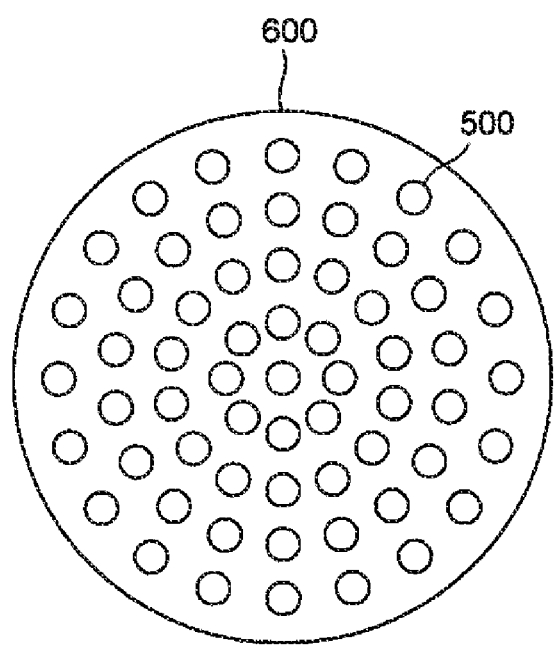

Referring to FIG. 16, a substrate 600 includes a plurality of dots 500, each of which may include first to third light emitting parts. With this configuration, it is possible to realize white light of daylight and warm white colors from each of the dots 500. Of course, the present invention is not limited to this configuration. For example, each of the dots 500 may include one of the first to third light emitting parts. In other words, dots including the first light emitting parts, dots including the second light emitting parts, and dots including the third light emitting parts may be located adjacent to one another in a repetitive manner. Alternatively, a region where the dots including the first light emitting parts aggregate densely, a region where the dots including the second light emitting parts aggregate densely, and a region where the dots including the third light emitting parts aggregate densely may be separated on the substrate. Alternatively, the second and third light emitting parts may be formed in a single dot. As such, arrangement of the light emitting parts may be variously set on the substrate depending on process convenience or desired products.

In the description of the embodiments, the first and second light emitting parts are provided to realize a daylight color and a warm white color with reference to a color temperature of 6000 K, respectively. However, the present invention is not limited to this configuration. For example, the first light emitting part may emit light having a higher color temperature than that of the second light emitting part. Preferably, the first and second light emitting parts are divided with reference to a color temperature in the range of 4000-6000 K. Thus, the light emitting device may include a first light emitting part emitting white light having a higher color temperature, a second light emitting part emitting white light having a lower color temperature, and a third light emitting part emitting light in the visible range of 580 nm or more, in which the second and third light emitting parts realize white light of a warm white color temperature of 3000 K or less. Accordingly, the present invention provides a light emitting device capable of realizing white light having various color temperatures.

As apparent from the above description, according to the present invention, the light emitting device includes a plurality of light emitting parts in a single package, thereby realizing white light having various spectra and color temperatures corresponding to desired mood and utility. In particular, the light emitting device of the invention is controlled to emit light having a suitable wavelength or a suitable color temperature depending on the circadian rhythm of humans, thereby enabling improvement of the user's health.

Further, the light emitting device of the present invention has the light emitting parts constituted in a single package, thereby simplifying a manufacturing process and reducing manufacturing costs while increasing space efficiency, as compared to the conventional technique wherein light emitting parts are separately constituted in different packages.

Moreover, the light emitting device of the present invention includes an LED chip capable of emitting light in the visible range of 580 nm or more, thereby realizing white light having a lower color temperature without significantly increasing power and amounts of phosphor.

Although various embodiments have been described with reference to the accompanying drawings, the present invention is not limited to the embodiments and the drawings. It should be understood that various modifications and changes can be made by those skilled in the art without departing from the spirit and scope of the present invention as defined by the accompanying claims.

The invention claimed is:

1. A light emitting device, comprising:
a first light emitting part comprising a first LED chip and a first phosphor, and emitting a daylight color having a color temperature of 6000 K or more;
a second light emitting part comprising a second LED chip and a second phosphor, and emitting white light having a color temperature less than 6000 K;
a third light emitting part comprising a third LED chip and emitting light in a visible range of 580 nm or more,
wherein the second and third light emitting parts are operable independently of the first light emitting part, and realize a warm white color having a color temperature of 3000 K or less with the white light emitted from the second light emitting part and the light emitted from the third light emitting part.

2. The light emitting device according to claim 1, wherein the first or second light emitting part comprises a phosphor represented by the following Chemical Formula 1:

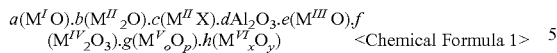  <Chemical Formula 1>

(where $M^I$ is at least one selected from the group consisting of Pb and Cu; $M^{II}$ is at least one selected from the group consisting of Li, Na, K, Rb, Cs, Au, and Ag; $M^{III}$ is at least one selected from the group consisting of Be, Mg, Ca, Sr, Ba, Zn, Cd, and Mn; $M^{IV}$ is at least one selected from the group consisting of Sc, B, Ga, and In; $M^V$ is at least one selected from the group consisting of Si, Ge, Ti, Zr, Mn, V, Nb, Ta, W, and Mo; $M^{VI}$ is at least one selected from the group consisting of Bi, Sn, Sb, Sc, Y, La, Ce, Pr, Nd, Pm, Sm, Eu, Gd, Tb, Dy, Ho, Er, Tm, Yb, and Lu; X is at least one selected from the group consisting of F, Cl, Br, and I; and a, b, c, d, e, f, g, o, p, h, x, and y are respectively set in the ranges of: $0<a\leq 2$, $0\leq b\leq 2$, $0\leq c\leq 2$, $0d\leq 8$, $0\leq e\leq 4$, $0\leq f\leq 3$, $0g\leq 8$, $1\leq o\leq 2$, $1\leq p\leq 5$, $0h\leq 2$, $1\leq x\leq 2$, and $1\leq y\leq 5$).

3. The light emitting device according to claim 1, wherein the first or second light emitting part comprises a phosphor represented by the following Chemical Formula 2:

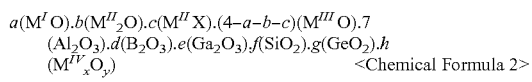  <Chemical Formula 2>

(where $M^I$ is at least one selected from the group consisting of Pb and Cu; $M^{II}$ is at least one selected from the group consisting of Li, Na, K, Rb, Cs, Au, and Ag; $M^{III}$ is at least one selected from the group consisting of Be, Mg, Ca, Sr, Ba, Zn, Cd, and Mn; $M^{IV}$ is at least one selected from the group consisting of Bi, Sn, Sb, Sc, Y, La, In, Ce, Pr, Nd, Pm, Sm, Eu, Gd, Tb, Dy, Ho, Er, Tm, Yb, and Lu; X is at least one selected from the group consisting of F, Cl, Br, and I; and a, b, c, d, e, f, g, h, x, and y are respectively set in the ranges of: $0<a\leq 4$, $0\leq b\leq 2$, $0\leq c\leq 2$, $0\leq d\leq 1$, $0\leq e\leq 1$, $0\leq f\leq 1$, $0\leq g\leq 1$, $0<h\leq 0.5$, $1\leq x\leq 2$, and $1\leq y\leq 5$).

4. The light emitting device according to claim 1, wherein the first or second light emitting part comprises a phosphor represented by the following Chemical Formula 3:

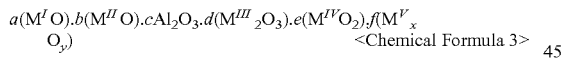  <Chemical Formula 3>

(where $M^I$ is at least one selected from the group consisting of Pb and Cu; $M^{II}$ is at least one selected from the group consisting of Be, Mg, Ca, Sr, Ba, Zn, Cd, and Mn; $M^{III}$ is at least one selected from the group consisting of B, Ga, and In; $M^{IV}$ is at least one selected from the group consisting of Si, Ge, Ti, Zr, and Hf; $M^V$ is at least one selected from the group consisting of Bi, Sn, Sb, Sc, Y, La, Ce, Pr, Nd, Pm, Sm, Eu, Gd, Tb, Dy, Ho, Er, Tm, Yb, and Lu; and a, b, c, d, e, f, x, and y are respectively set in the ranges of: $0<a\leq 1$, $0\leq b\leq 2$, $0<c\leq 8$, $0\leq d\leq 1$, $0\leq e\leq 1$, $0<f\leq 2$, $1\leq x\leq 2$, and $1\leq y\leq 5$).

5. The light emitting device according to claim 1, wherein the first or second light emitting part comprises a phosphor represented by the following Chemical Formula 4:

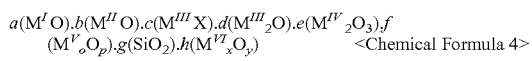  <Chemical Formula 4>

(where $M^I$ is at least one selected from the group consisting of Pb and Cu; $M^{II}$ is at least one selected from the group consisting of Be, Mg, Ca, Sr, Ba, Zn, Cd, and Mn; $M^{III}$ is at least one selected from the group consisting of Li, Na, K, Rb, Cs, Au, and Ag; $M^{IV}$ is at least one selected from the group consisting of Al, Ga, In, and B; $M^V$ is at least one selected from the group consisting of Ge, V, Nb, Ta, W, Mo, Ti, Zr, Hf, and P; $M^{VI}$ is at least one selected from the group consisting of Bi, Sn, Sb, Sc, Y, La, Ce, Pr, Nd, Pm, Sm, Eu, Gd, Tb, Dy, Ho, Er, Tm, Yb, and Lu; X is at least one selected from the group consisting of F, Cl, Br, and I; and a, b, c, d, e, f, g, h, o, p, x, and y are respectively set in the ranges of: $0<a\leq 2$, $0<b\leq 8$, $0\leq c\leq 4$, $0\leq d\leq 2$, $0\leq e\leq 2$, $0\leq f\leq 2$, $0\leq g\leq 10$, $0\leq h\leq 5$, $1\leq o\leq 2$, $1\leq p\leq 5$, $1\leq x\leq 2$, and $1\leq y\leq 5$).

6. The light emitting device according to claim 1, wherein the first or second light emitting part comprises a phosphor represented by the following Chemical Formula 5:

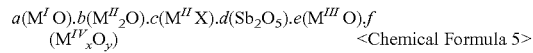  <Chemical Formula 5>

(where $M^I$ is at least one selected from the group consisting of Pb and Cu; $M^{II}$ is at least one selected from the group consisting of Li, Na, K, Rb, Cs, Au, and Ag; $M^{III}$ is at least one selected from the group consisting of Be, Mg, Ca, Sr, Ba, Zn, Cd, and Mn; $M^{IV}$ is at least one selected from the group consisting of Bi, Sn, Sc, Y, La, Pr, Sm, Eu, Tb, Dy, and Gd; X is at least one selected from the group consisting of F, Cl, Br, and I; and a, b, c, d, e, f, x, and y are respectively set in the ranges of: $0<a\leq 2$, $0\leq b\leq 2$, $0\leq c\leq 4$, $0<d\leq 8$, $0\leq e\leq 8$, $0\leq f\leq 2$, $1\leq x\leq 2$, and $1\leq y\leq 5$).

7. The light emitting device according to claim 1, wherein the first or second light emitting part comprises a phosphor represented by the following Chemical Formula 6:

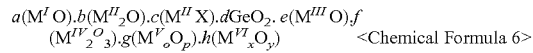  <Chemical Formula 6>

(where $M^I$ is at least one selected from the group consisting of Pb and Cu; $M^{II}$ is at least one selected from the group consisting of Li, Na, K, Rb, Cs, Au, and Ag; $M^{III}$ is at least one selected from the group consisting of Be, Mg, Ca, Sr, Ba, Zn, and Cd; $M^{IV}$ is at least one selected from the group consisting of Sc, Y, B, Al, Ga, In, and La; $M^V$ is at least one selected from the group consisting of Si, Ti, Zr, Mn, V, Nb, Ta, W, and Mo; $M^{VI}$ is at least one selected from the group consisting of Bi, Sn, Pr, Sm, Eu, Gd, and Dy; X is at least one selected from the group consisting of F, Cl, Br, and I; and a, b, c, d, e, f, g, h, o, p, x, and y are respectively set in the ranges of: $0<a\leq 2$, $0\leq b\leq 2$, $0\leq c\leq 10$, $0<d\leq 10$, $0\leq e\leq 14$, $0\leq f\leq 14$, $0\leq g\leq 10$, $0\leq h\leq 2$, $1\leq o\leq 2$, $1\leq p\leq 5$, $1\leq x\leq 2$, and $1\leq y\leq 5$).

8. The light emitting device according to claim 1, wherein the first or second light emitting part comprises a phosphor represented by the following Chemical Formula 7:

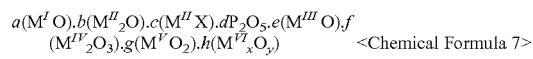  <Chemical Formula 7>

(where $M^I$ is at least one selected from the group consisting of Pb and Cu; $M^{II}$ is at least one selected from the group consisting of Li, Na, K, Rb, Cs, Au, and Ag; $M^{III}$ is at least one selected from the group consisting of Be, Mg, Ca, Sr, Ba, Zn, Cd, and Mn; $M^{IV}$ is at least one selected from the group consisting of Sc, Y, B, Al, La, Ga, and In; $M^V$ is at least one selected from the group consisting of Si, Ge, Ti, Zr, Hf, V, Nb, Ta, W, and Mo; $M^{VI}$ is at least one selected from the group consisting of Bi, Sn, Pr, Sm, Eu, Gd, Dy, Ce, and Tb; X is at least one selected from the group consisting of F, Cl, Br, and I; and a, b, c, d, e, f, g, h, x, and y are respectively set in the ranges of: $0<a\leq 2$, $0\leq b\leq 12$, $0\leq c\leq 16$, $0<d\leq 3$, $0\leq e\leq 5$, $0\leq f\leq 3$, $0\leq g\leq 2$, $0\leq h\leq 2$, $1\leq x\leq 2$, and $1\leq y\leq 5$).

9. The light emitting device according to claim 1, wherein the first or second light emitting part comprises a plurality of phosphors.

10. The light emitting device according to claim 1, wherein the first and second LED chips emit blue or UV light.

11. The light emitting device according to claim 1, further comprising:
a controller to control voltage applied to at least one of the first, second, and third light emitting parts.

12. The light emitting device according to claim 11, wherein the controller adjusts the externally input voltage according to time.

13. The light emitting device according to claim 12, wherein the controller adjusts the externally input voltage on a 24-hour cycle.

14. The light emitting device according to claim 1, wherein the first to third light emitting parts are formed in a single package.

15. The light emitting device according to claim 14,
wherein the package comprises a substrate upon which the first to third light emitting parts are mounted, and
wherein the phosphors of the first and second light emitting parts are disposed above the first and second LED chips, respectively.

16. The light emitting device according to claim 14,
wherein the package further comprises a heat sink to dissipate heat generated from the LED chips,
wherein the first to third LED chips are disposed above the heat sink, and
wherein the phosphors of the first and second light emitting parts are disposed above the first and second LED chips, respectively.

17. The light emitting device according to claim 14, wherein the second light emitting part is disposed nearer a center of the package than the first and third light emitting parts.

18. A light emitting device, comprising:
a first light emitting part comprising a first LED chip and a first phosphor, and emitting white light having a higher color temperature;
a second light emitting part comprising a second LED chip and a second phosphor, and emitting white light having a lower color temperature; and
a third light emitting part including a third LED chip emitting light in a visible range of 580 nm or more,
wherein the second and third light emitting parts are operable independently of the first light emitting part, and realize a warm white color having a color temperature of 3000 K or less with the white light emitted from the second light emitting part and the light emitted from the third light emitting part.

* * * * *

UNITED STATES PATENT AND TRADEMARK OFFICE
CERTIFICATE OF CORRECTION

Page 1 of 1

PATENT NO. : 7,679,281 B2
APPLICATION NO. : 12/051637
DATED : March 16, 2010
INVENTOR(S) : Do Hyung Kim et al.

It is certified that error appears in the above-identified patent and that said Letters Patent is hereby corrected as shown below:

Title page Item (30) Foreign Application Priority Data, the application Number reading "10-2006-0026750" should read -- 10-2007-0026750 --.

Signed and Sealed this
First Day of February, 2011

David J. Kappos
*Director of the United States Patent and Trademark Office*